United States Patent
Maimon et al.

(10) Patent No.: US 10,925,730 B2
(45) Date of Patent: Feb. 23, 2021

(54) PAPILLARY MUSCLE ADJUSTMENT

(71) Applicant: Edwards Lifesciences Corporation, Irvine, CA (US)

(72) Inventors: David Maimon, Haifa (IL); Noam Nir, Gesher Haziv (IL); Tomer Saar, Pardes Hanna-Karkur (IL)

(73) Assignee: Edwards Lifesciences Corporation, Irvine, CA (US)

( * ) Notice: Subject to any disclaimer, the term of this patent is extended or adjusted under 35 U.S.C. 154(b) by 255 days.

(21) Appl. No.: 15/956,031

(22) Filed: Apr. 18, 2018

(65) Prior Publication Data

US 2018/0303613 A1     Oct. 25, 2018

Related U.S. Application Data

(60) Provisional application No. 62/489,817, filed on Apr. 25, 2017.

(51) Int. Cl.
    *A61F 2/24*     (2006.01)

(52) U.S. Cl.
    CPC ............ *A61F 2/2454* (2013.01); *A61F 2/243* (2013.01); *A61F 2/2466* (2013.01); *A61F 2/2487* (2013.01); *A61F 2/2457* (2013.01); *A61F 2002/249* (2013.01)

(58) Field of Classification Search
    CPC ............... A61F 2/2451; A61F 2/2454; A61F 2002/249; A61F 2/2457; A61F 2/243; A61F 2/2466; A61F 2/2487; A61M 29/00; A61M 29/02; A61B 2017/00243
    USPC ........................................ 606/192; 623/2.11
    See application file for complete search history.

(56) References Cited

U.S. PATENT DOCUMENTS

| | | | |
|---|---|---|---|
| 6,723,038 B1 | 4/2004 | Schroeder et al. | |
| 7,955,247 B2 | 6/2011 | Levine et al. | |
| 8,206,439 B2 | 6/2012 | Gomez Duran | |
| 9,060,858 B2 | 6/2015 | Thornton et al. | |
| 9,125,742 B2 | 9/2015 | Yoganathan et al. | |
| 2005/0187620 A1 | 8/2005 | Pai et al. | |
| 2006/0281968 A1 | 12/2006 | Duran et al. | |
| 2008/0249618 A1 | 10/2008 | Huynh et al. | |
| 2008/0269876 A1 | 10/2008 | Huynh et al. | |
| 2008/0293996 A1* | 11/2008 | Evans | A61B 17/12195 600/16 |
| 2009/0222081 A1 | 9/2009 | Linder et al. | |

(Continued)

OTHER PUBLICATIONS

Hung et al., "A novel approach for reducing ischemic mitral regurgitation by injection of a polymer to reverse remodel and reposition displaced papillary muscles." Circulation. Sep. 30, 2008;118(14 Suppl):S263-9.

(Continued)

*Primary Examiner* — Wade Miles
*Assistant Examiner* — Kankindi Rwego
(74) *Attorney, Agent, or Firm* — Chang & Hale LLP

(57) ABSTRACT

A method for improving leaflet prolapse and/or valve regurgitation associated with a heart valve involves delivering a spacer device into a ventricle of a heart using a delivery system comprising a catheter, fixing the spacer device to a wall of the ventricle, expanding the spacer device to reposition a papillary muscle disposed in the ventricle away from the wall, the papillary muscle being connected to a leaflet of an atrioventricular heart valve via chordae tendineae, and releasing the spacer device from the catheter.

18 Claims, 8 Drawing Sheets

(56) References Cited

U.S. PATENT DOCUMENTS

| | | |
|---|---|---|
| 2015/0025553 A1 | 1/2015 | Del Nido et al. |
| 2016/0015877 A1 | 1/2016 | Guerrero et al. |
| 2016/0022417 A1* | 1/2016 | Karapetian ........... A61F 2/2418 623/2.38 |

OTHER PUBLICATIONS

Hung et al., "Persistent Reduction of Ischemic Mitral Regurgitation by Papillary Muscle Repositioning. Structural Stabilization of the Papillary Muscle-Ventricular Wall Complex." Circulation. Sep. 11, 2007;116(11 Suppl):I259-63.

Hvass, Ulrik, "Papillary Muscle Sling: A New Functional Approach to Mitral Repair in Patients with Ischemic Left Ventricular Dysfunction and Functional Mitral Regurgitation." The Annals of Thoracic Surgery, vol. 75, Issue 3, Mar. 2003, pp. 809-811.

Lafci, Gokhan, MD., et al., "Papillary Muscle Repositioning as a Subvalvular Apparatus Preservation Technique." Texas Heart Institute Journal, vol. 41, No. 1, 2014.

Langer, Frank, MD, et al., "RING plus STRING: Papillary muscle repositioning as an adjunctive repair technique for ischemic mitral regurgitation." The Journal of Thoracic and Cardiovascular Surgery, vol. 133, No. 1, 2007.

Solis, Jorge et al., "Polymer Injection Therapy to Reverse Remodel the Papillary Muscles: Efficacy in Reducing Mitral Regurgitation in a Chronic Ischemic Model." Circ Cardiovasc Interv. Oct. 2010; 3(5): 499-505.

\* cited by examiner

PAPILLARY MUSCLE ADJUSTMENT

CROSS-REFERENCE TO RELATED APPLICATIONS

This application claims the benefit of U.S. Application No. 62/489,817, filed Apr. 25, 2017, which is incorporated herein by reference.

BACKGROUND

Field

The present disclosure generally relates to the field of valve correction.

Description of Related Art

Heart valve dysfunction can result in regurgitation and other complications due to valve prolapse from failure of valve leaflets to properly coapt. For atrioventricular valves, papillary muscle position can affect the ability of valve leaflets to function properly.

SUMMARY

In some implementations, the present disclosure relates to a method for treating a heart valve. The method comprises delivering a spacer device into a ventricle of a heart using a delivery system comprising a catheter, fixing the spacer device to a wall of the ventricle, expanding the spacer device to reposition a papillary muscle disposed in the ventricle away from the wall, the papillary muscle being connected to a leaflet of an atrioventricular heart valve via chordae tendineae, and releasing the spacer device from the catheter. The spacer may close the gap between the leaflets by moving the papillary muscles. Performing the method may thus improve at least one of prolapse of the leaflet and regurgitation of the heart valve. In certain embodiments, the ventricle is a left ventricle of the heart and the heart valve is a mitral valve.

The method may further comprise, after said expanding the spacer device, determining whether function of the heart valve is adequate, and when it is determined that the function of the heart valve is not adequate, adjusting the spacer device prior to said releasing the spacer device from the catheter. For example, determining whether function of the heart valve is adequate may involve determining whether the papillary muscle has moved to a desirable position. Determining whether function of the heart valve is adequate may involve determining whether regurgitation of the heart valve has been sufficiently reduced. In certain embodiments, determining whether function of the heart valve is adequate comprises determining whether a position of the leaflet has moved to a desirable position. Adjusting the spacer device may comprise further expanding the spacer device to further reposition the papillary muscle.

In certain embodiments, the spacer device comprises a balloon, and expanding the spacer device comprises filling the balloon with fluid. For example, the fluid may comprises saline. The method may comprise, after said filling the balloon with fluid, determining whether function of the heart valve is adequate. When it is determined that the function of the heart valve is not adequate, the method may involve adjusting an amount of fluid in the balloon. When it is determined that the function of the heart valve is adequate, the method may comprise at least partially replacing the fluid with a polymer. Determining whether function of the heart valve is adequate may be performed at least part using echocardiography.

Fixing the spacer device to the wall of the ventricle may involve inserting an anchor coupled to the spacer device into myocardium tissue associated with the wall. In certain embodiments, the method further comprises at least partially surrounding the papillary muscle with the spacer device. The spacer device may comprises a collar form. Delivering the spacer device into the ventricle of the heart may be performed using a transcatheter procedure. For example, the transcatheter procedure is a transfemoral procedure.

In some implementations, the present disclosure relates to a method for treating a heart valve. The method may involve delivering a strap device into a ventricle of a heart using a delivery system comprising a catheter, wrapping the strap device at least partially around a papillary muscle disposed in the ventricle, the papillary muscle being connected to a leaflet of an atrioventricular heart valve of the heart via chordae tendineae, fixing the strap device to a wall of the ventricle, and releasing the strap device from the catheter. Performing the method improves at least one of prolapse of the leaflet and regurgitation of the heart valve. In certain embodiments, the ventricle is a left ventricle of the heart and the heart valve is a mitral valve.

The method may further comprise, after said fixing the strap device, determining whether function of the heart valve is adequate, and when it is determined that the function of the heart valve is not adequate, adjusting the strap device prior to said releasing the strap device from the catheter. Determining whether function of the heart valve is adequate may involve determining whether the papillary muscle has moved to a desirable position. Determining whether function of the heart valve is adequate may involve determining whether regurgitation of the heart valve has been sufficiently reduced. Determining whether function of the heart valve is adequate may involve determining whether a position of the leaflet has moved to a desirable position. In certain embodiments, adjusting the strap device comprises adjusting a tension of the strap device to further reposition the papillary muscle. Determining whether function of the heart valve is adequate may be performed at least part using echocardiography.

In certain embodiments, the strap device comprises a band form, and said fixing the strap device to the wall of the ventricle comprises fixing one or more end portions of the band form to the wall of the ventricle. Fixing the strap device to the wall of the ventricle may involve inserting an anchor coupled to the strap device into myocardium tissue associated with the wall. Delivering the strap device into the ventricle of the heart may be performed using a transcatheter procedure. For example, the transcatheter procedure may be a transfemoral procedure.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

Figure 1:
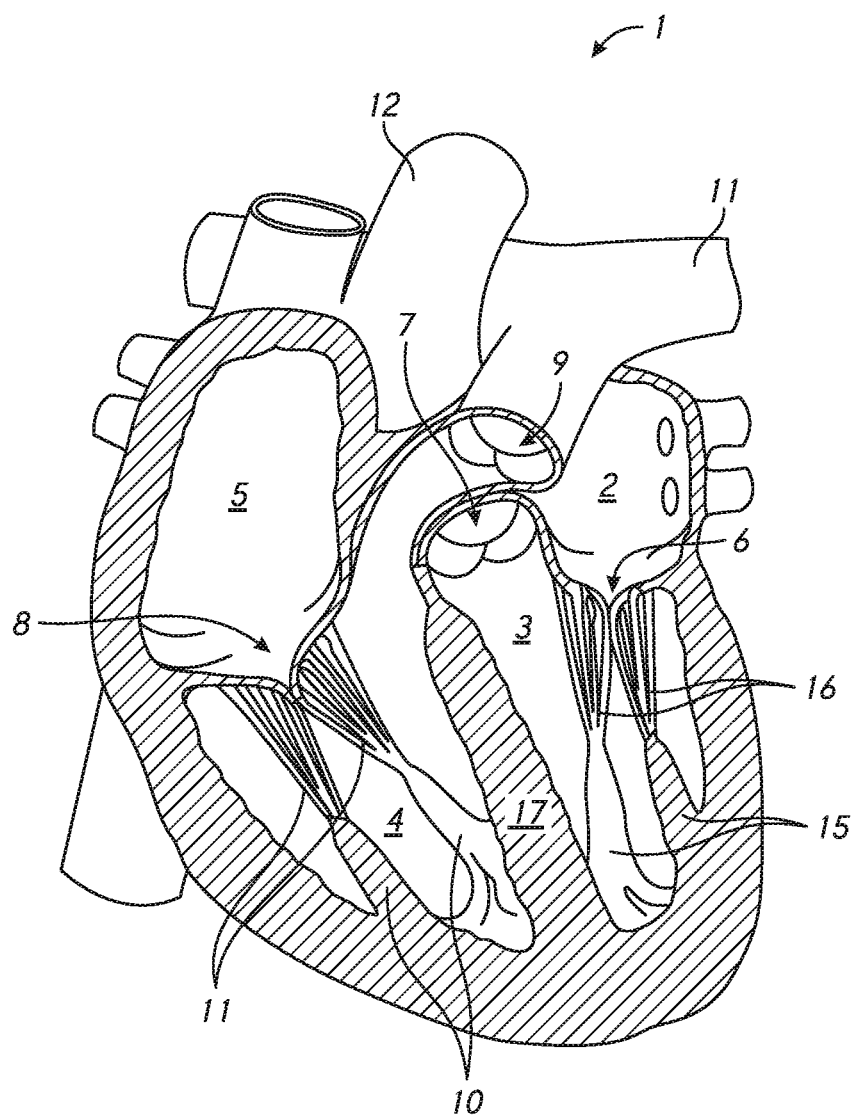
FIG. 1 provides a cross-sectional view of a human heart.

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. A wall of muscle 17, referred to as the septum, separates the left 2 and right 5 atria and the left 3 and right 4 ventricles. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11, and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant, and press back against the leaflets. As a result, the leaflets/cusps come in apposition to each other, thereby closing the flow passage.

The atrioventricular (i.e., mitral and tricuspid) heart valves may further comprise a collection of chordae tendineae and papillary muscles for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets (two shown in FIG. 1) and three corresponding papillary muscles 10 (two shown in FIG. 1). The leaflets of the tricuspid valve may be referred to as the anterior, posterior and septal leaflets, respectively. The valve leaflets are connected to the papillary muscles by the chordae tendineae 11, which are disposed in the right ventricle 4 along with the papillary muscles 10. Although tricuspid valves are described herein as comprising three leaflets, it should be understood that tricuspid valves may occur with two or four leaflets in certain patients and/or conditions; the principles relating to papillary muscle adjustment disclosed herein are applicable to atrioventricular valves having any number of leaflets and/or papillary muscles associated therewith.

The right ventricular papillary muscles 10 originate in the right ventricle wall, and attach to the anterior, posterior and septal leaflets of the tricuspid valve, respectively, via the chordae tendineae 11. The papillary muscles 10 of the right ventricle 4 may have variable anatomy; the anterior papillary may generally be the most prominent of the papillary muscles. The papillary muscles 10 may serve to secure the leaflets of the tricuspid valve 8 to prevent prolapsing of the leaflets into the right atrium 5 during ventricular systole. Tricuspid regurgitation can be the result of papillary dysfunction or chordae rupture.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

The valve leaflets of the mitral valve 6 may be prevented from prolapsing into the left atrium 2 by the action of the chordae tendineae 16 tendons connecting the valve leaflets to the papillary muscles 15. The relatively inelastic chordae tendineae 16 are attached at one end to the papillary muscles 15 and at the other to the valve leaflets; chordae tendineae from each of the papillary muscles 15 are attached to a respective leaflet of the mitral valve 6. Thus, when the left ventricle 3 contracts, the intraventricular pressure forces the valve to close, while the chordae tendineae 16 keep the leaflets coapting together and prevent the valve from opening in the wrong direction, thereby preventing blood to flow back to the left atrium 2. The various chords of the chordae tendineae may have different thicknesses, wherein relatively thinner chords are attached to the free leaflet margin, while relatively thicker chords (e.g., strut chords) are attached farther away from the free margin.

Figure 2:
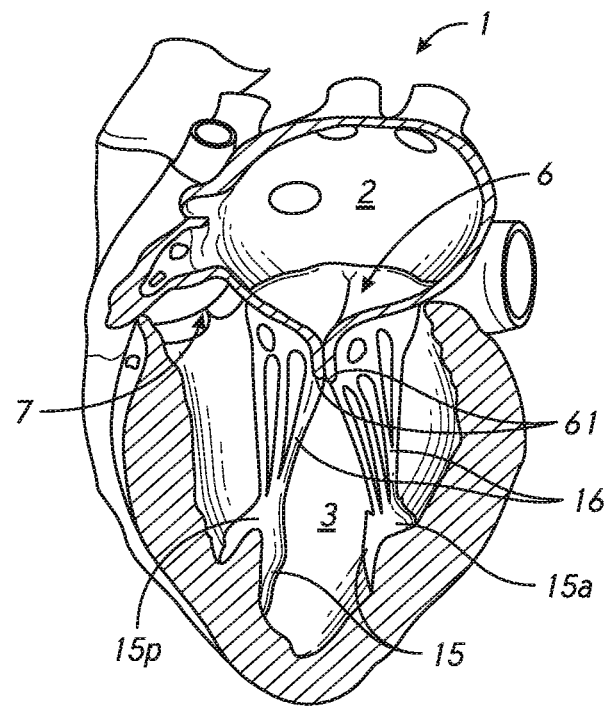
FIG. 2 provides a cross-sectional view of the left ventricle and left atrium of an example heart.

FIG. 2 provides a cross-sectional view of the left ventricle 3 and left atrium 2 of an example heart 1. The diagram of FIG. 2 shows the mitral valve 6, wherein the disposition of the valve 6, papillary muscles 15 and/or 16 may be illustrative as providing for proper coapting of the valve leaflets to advantageously at least partially prevent regurgitation and/or undesirable flow into the left atrium from the left ventricle 3 and vice versa. Although a mitral valve 6 is shown in FIG. 2 and various other figures provided herewith and described herein in the context of certain embodiments of the present disclosure, it should be understood that papillary muscle adjustment principles disclosed herein may be applicable with respect to any atrioventricular valve and associated anatomy (e.g., papillary muscles, chordae tendineae, ventricle wall, etc.), such as the tricuspid valve.

As described above, with respect to a healthy heart valve as shown in FIG. 2, the valve leaflets 61 may extend inward from the valve annulus and come together in the flow orifice to permit flow in the outflow direction (e.g., the downward direction in FIG. 2) and prevent backflow or regurgitation toward the inflow direction (e.g., the upward direction in FIG. 2). For example, during atrial systole, blood flows from the atria 2 to the ventricle 3 down the pressure gradient, resulting in the chordae tendineae 16 being relaxed due to the atrioventricular valve 6 being forced open. When the ventricle 3 contracts during ventricular systole, the increased blood pressures in both chambers may push the valve 6 closed, preventing backflow of blood into the atria 2. Due to the lower blood pressure in the atria compared to the ventricles, the valve leaflets may tend to be drawn toward the atria. The chordae tendineae 16 can serve to tether the leaflets and hold them in a closed position when they become tense during ventricular systole. The papillary muscles 15 provide structures in the ventricles for securing the chordae tendineae and therefore allowing the chordae tendineae to hold the leaflets in a closed position. The papillary muscles 15 may include an anterolateral papillary muscle 15a, which may be tethered to the posterior leaflet, for example, and a posteromedial papillary muscle 15p, which may be tethered to the anterior leaflet, for example. With respect to the state of the heart 1 shown in FIG. 2, the proper coaptation of the valve leaflets, which may be due in part to proper position of the papillary muscles 15, may advantageously result in mitral valve operation substantially free of leakage.

Figure 3:
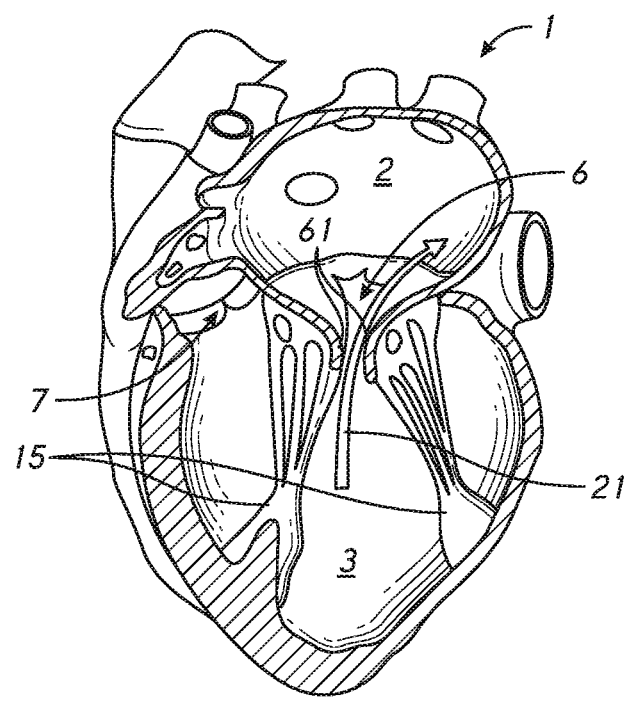
FIG. 3 provides a cross-sectional view of a heart experiencing mitral regurgitation.

Heart valve disease represents a condition in which one or more of the valves of the heart fails to function properly. Diseased heart valves may be categorized as stenotic, wherein the valve does not open sufficiently to allow adequate forward flow of blood through the valve, and/or incompetent, wherein the valve does not close completely, causing excessive backward flow of blood through the valve when the valve is closed. In certain conditions, valve disease can be severely debilitating and even fatal if left untreated. With regard to incompetent heart valves, over time and/or due to various physiological conditions, the position of papillary muscles may become altered, thereby potentially contributing to valve regurgitation. For example, as shown in FIG. 3, which illustrates a cross-sectional view of a heart 1 experiencing mitral regurgitation flow 21, dilation of the left ventricle may cause changes in the position of the papillary muscles 15 that allow flow 21 back from the ventricle 3 to the atrium 2. Dilation of the left ventricle can be causes by any number of conditions, such as focal myocardial infarction, global ischemia of the myocardial tissue, or idiopathic dilated cardiomyopathy, resulting in alterations in the geometric relationship between papillary muscles and other components associated with the valve(s) that can cause valve regurgitation. Functional regurgitation may further be present even where the valve components may be normal pathologically, yet may be unable to function properly due to changes in the surrounding environment. Examples of such changes include geometric alterations of one or more heart chambers and/or decreases in myocardial contractility. In any case, the resultant volume overload that exists as a result of an insufficient valve may increase chamber wall stress, which may eventually result in a dilatory effect that causes papillary muscle alteration resulting in valve dysfunction and degraded cardiac efficiency.

With further reference to FIG. 3, the heart 1 is shown in a state where functional mitral valve regurgitation is present. Functional mitral valve regurgitation may be considered a disease of the left ventricle 3, rather than of the mitral valve 6. For example, mitral valve regurgitation may occur when the left ventricle 3 of the heart 1 is distorted or dilated, displacing the papillary muscles 15 that support the two valve leaflets 61. The valve leaflets 61 therefore may no longer come together sufficiently to close the annulus and prevent blood flow back into the atrium 2. If left untreated, the functional mitral valve regurgitation experienced in the state shown in FIG. 3 may overload the heart 1 and can possibly lead to or accelerate heart failure. Solutions presented herein provide devices and methods for moving the papillary muscles 15 closer to their previous position, which may advantageously reduce the occurrence of mitral regurgitation.

As shown in FIG. 3, the leaflets 61 of the mitral valve (or tricuspid valve) are not in a state of coaptation, resulting in an opening between the mitral valve leaflets 61 during the systolic phase of the cardiac cycle, which allows the leakage flow 21 of fluid back up into the atrium 2. The papillary muscles 15 may be displaced due to dilation of the left ventricle 3, or due to one or more other conditions, as described above, which may contribute to the failure of the valve 6 to close properly. The failure of the valve leaflets 61 to coapt properly may result in unwanted flow in the outflow direction (e.g., the upward direction in FIG. 3) and/or unwanted backflow or regurgitation toward the inflow direction (e.g., the downward direction in FIG. 2).

Certain embodiments disclosed herein provide solutions for incompetent heart valves that involve papillary muscle re-positioning and/or adjustment. Solutions presented herein may be used to at least partially change the position of one or more papillary muscles in order to reduce the occurrences and/or severity of regurgitation, such as mitral regurgitation. Mitral valve regurgitation often may be driven by the functional/physical positioning changes described above, which may cause papillary muscle displacement and/or dilatation of the valve annulus. As the papillary muscles move away from the valve annulus, the chordae connecting the muscles to the leaflets may become tethered. Such tethering may restrict the leaflets from closing together, either symmetrically or asymmetrically, depending on the relative degree of displacement between the papillary muscles. Moreover, as the annulus dilates in response to chamber enlargement and increased wall stress, increases in annular area and changes in annular shape may increase the degree of valve insufficiency.

Various techniques that suffer from certain drawbacks may be implemented for treating mitral valve dysfunction, including surgical repair or replacement of the diseased valve or medical management of the patient, which may be appropriate/effective primarily in early stages of mitral valve dysfunction, during which levels of regurgitation may be relatively low. For example, such medical management may generally focus on volume reductions, such as diuresis or afterload reducers, such as vasodilators, for example. Valve replacement operations may also be used to treat regurgitation from valve dysfunction. However, such operations can result in ventricular dysfunction or failure following surgery. Further limitations to valve replacement solutions may include the potential need for lifelong therapy with powerful anticoagulants in order to mitigate the thromboembolic potential of prosthetic valve implants. Moreover, in the case of biologically-derived devices, such as those used as mitral valve replacements, the long-term durability may be limited. Another commonly employed repair technique involves the use of annuloplasty rings to improve mitral valve function. An annuloplasty ring may be placed in the valve annulus and the tissue of the annulus sewn or otherwise secured to the ring. Annuloplasty rings can provide a reduction in the annular circumference and/or an increase in the leaflet coaptation area. However, annuloplasty rings may flatten the saddle-like shape of the valve and/or hinder the natural contraction of the valve annulus. In addition, various surgical techniques may be used to treat valve dysfunction. However, such techniques may suffer from various limitations, such as requiring opening the heart to gain direct access to the valve and the valve annulus. Therefore, cardiopulmonary bypass may be required, which may introduce additional morbidity and mortality to the surgical procedures. Additionally, for surgical procedures, it can be difficult or impossible to evaluate the efficacy of the repair prior to the conclusion of the operation.

Disclosed herein are devices and methods for treating valve dysfunction without the need for cardiopulmonary bypass and without requiring major remodeling of the dysfunctional valve. In particular, passive techniques to change the shape and/or position of the papillary muscles are disclosed for reducing regurgitation while maintaining substantially normal leaflet anatomy. Further, various embodiments disclosed herein provide for the treatment of valve dysfunction that can be executed on a beating heart, thereby allowing for the ability to assess the efficacy of the papillary muscle re-positioning treatment and potentially implement modification thereto without the need for bypass support.

Papillary Muscle Adjustment

Certain embodiments disclosed herein provide for systems, devices and methods for adjusting the position of papillary muscles in the left and/or right ventricles of a heart in order to improve valve coaptation during ventricular systole. For example, papillary adjustment devices are disclosed that may be implanted independently in one of the ventricles of the heart. Such devices may be introduced into the patient system through surgical or, advantageously, minimally-invasive means.

Figure 4:
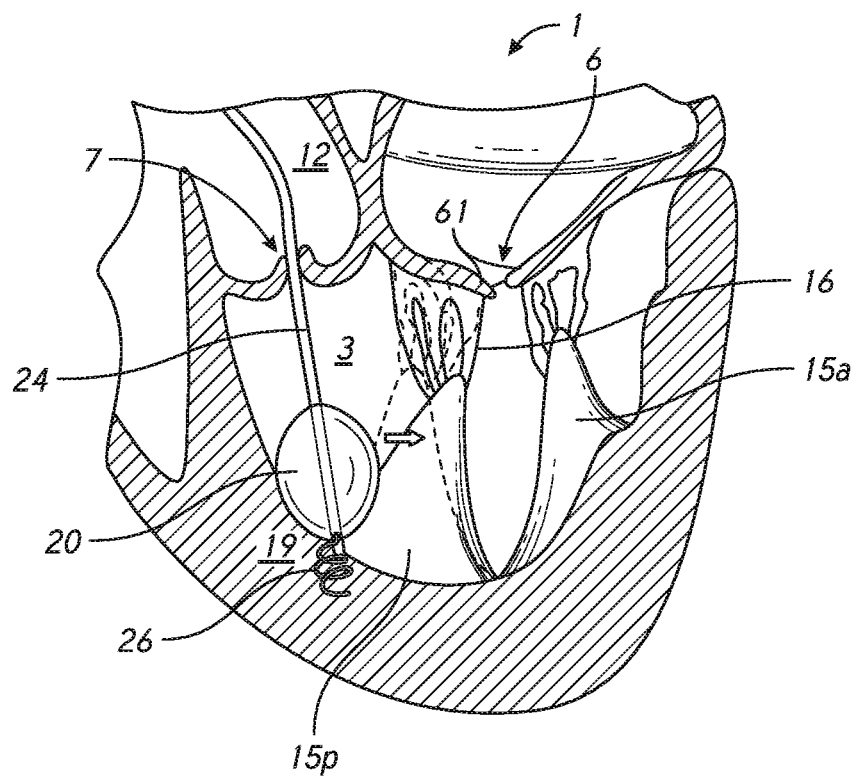
FIG. 4 illustrates a cross-section of a heart having a papillary muscle adjustment system disposed therein according to one or more embodiments.

FIG. 4 illustrates a cross-section of a heart 1 showing a left ventricle 3 thereof. Although certain disclosure herein is presented in the context of the left ventricle and associated anatomy (e.g., valves, papillary muscles, chordae tendineae, ventricle wall, etc.), it should be understood that the principles disclosed herein may be applicable in any ventricle of the heart (e.g., right ventricle) and associated anatomy (e.g., tricuspid valve, papillary muscles, chordae tendineae, ventricle wall, etc.). As described above, in a normal heart, the papillary muscles may contract during the heart cycle to assist in maintaining proper valve function. Reductions in, or failure of, the papillary muscle function can contribute to valve dysfunction and/or regurgitation, which may be caused by infarction at or near the papillary muscle, ischemia, or other causes, such as idiopathic dilated cardiomyopathy, for example.

FIG. 4 shows a papillary muscle adjustment spacer device 20, which may be implanted in the left ventricle 3 (or right ventricle in another embodiment) to at least partially displace the papillary muscle 15p away from the ventricle wall 19. In certain conditions/patients, the displacement of the papillary muscle 15p from the ventricle wall 19 may help correct mitral valve insufficiency due to dysfunction or rupture of the papillary muscle.

With respect to embodiments in which the papillary muscle adjustment spacer device 20 is implanted in the right ventricle, the device may serve to correct tricuspid regurgitation, which, similar to mitral regurgitation, involves a disorder in which the tricuspid valve does not close tight enough to prevent backflow through the valve. During tricuspid regurgitation, blood may flow backward into the right atrium when the right ventricle contracts. Such tricuspid valve dysfunction may result from the increase in size of the right ventricle. For example, enlargement or dilation of the right ventricle may result from high blood pressure in the arteries of the lungs, or from other heart problems, such as poor squeezing of the left side of the heart, or from problems with the opening or closing of another one of the heart valves.

The placement of the device 20 between the ventricle wall 19 and the papillary muscle 15p may cause the papillary muscle 15p to reposition inward, thereby lessening the traction of the chordae tendineae on the corresponding leaflet of the mitral valve, thereby resulting in improved coaptation of the mitral valve leaflets during closure of the valve. Although FIG. 4 shows repositioning of the posterior-medial papillary muscle 15*p*, it should be appreciated that the device 20 could similarly be used to reposition the anterolateral papillary muscle 15*a*.

The delivery system for the spacer device 20 may include a catheter 24 for navigating the device 20 to the desired position. For example, the device 20 may be delivered to the implantation location in an at least partially collapsed or contracted state, wherein the device 20 may be inflated or expanded upon arrival in the implant chamber, such as a ventricle of the heart. The device 20 may be inserted non-surgically in, for example, a transcatheter procedure (e.g., transfemoral, transseptal, transapical, etc.), wherein the device 20 is inserted into the left ventricle 3 from the aorta 12 through the aortic valve 7 and positioned behind one of the papillary muscles (e.g., posteromedial papillary muscle 15*p*). With respect to right ventricle papillary muscle adjustment, the device 20 may be inserted into the right ventricle from the pulmonary artery through the pulmonary valve and positioned behind one of the papillary muscles of the right ventricle. In certain embodiments, the device 20 is a spacer form, such as a balloon or the like.

The spacer device 20 may be fixed to the myocardium tissue of the wall of the left ventricle. In certain embodiments, the spacer device 20 may be fixed to the left ventricle wall using an anchor or attachment member 26. Once positioned and/or fixed, the spacer device 20 may be expanded or inflated to a desirable size. For example, the device 20 may comprise a balloon that may be filled with fluid, such as a saline solution or a gaseous solution, through the catheter 24. In certain embodiments, the desired position of the spacer device 20 and/or the amount of expansion of the device 20 through fluid infusion or other means may be determined by the resulting movement of the papillary muscle and/or the reduction in mitral (or tricuspid) regurgitation performance, which may be observed using echocardiography or other means. With regard to a fluid-filled spacer device, when it is determined that the result is satisfactory, the fluid (e.g., saline solution) may be replaced with an injected polymer or other substance providing desirable firmness.

Figure 5:
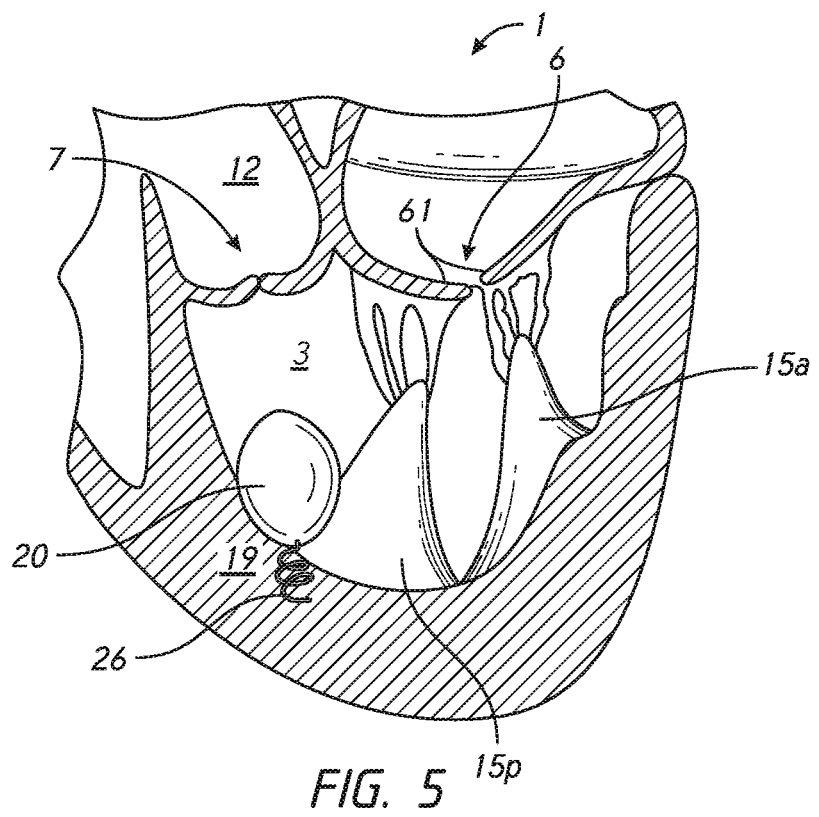
FIG. 5 illustrates a cross-section of a heart having a papillary muscle adjustment spacer device implanted therein according to one or more embodiments.

FIG. 5 shows a papillary muscle adjustment spacer device 20 in a fixed position in the left ventricle 3 (or right ventricle in another embodiment) and maintaining space between a papillary muscle (e.g., papillary muscle 15*p*) and the ventricle wall 19. The spacer device 20 is illustrated in FIG. 5 as released from the delivery system shown in FIG. 4.

The spacer device 20 may be fixed to the ventricle wall (e.g., myocardium) in any suitable or desirable way. For example, the device 20 may be sutured to the ventricle wall, or anchored using a barb-like hook or corkscrew structure, or other type of anchor that may be attached to, or embedded in, the tissue of the ventricle wall. Placement of the spacer device 20 and/or degree of device (e.g., balloon) inflation/expansion can be guided in place using echocardiography to observe whether reduced mitral regurgitation and/or desired leaflet seating is produced thereby. It may be desirable to inject a minimal amount of fluid into the device 20 that achieves a satisfactory or desirable result with respect to regurgitation and/or leaflet seating in order to reduce/minimize obstruction introduced by the spacer device 20. In certain embodiments, the device 20 may be injected with fluid in discrete increments (e.g., increments of between 0-10 mL or greater). By observing the performance and/or physical structure of the atrioventricular valve and/or associated anatomy (e.g., papillary muscle(s)), papillary muscle adjustment methods disclosed here may advantageously allow for substantially immediate or real-time adjustment of the device position and/or volume while the delivery system is locally disposed and available for adjustment operations.

Although spacer balloon devices are disclosed herein in the context of certain embodiments, it should be understood that papillary muscle adjustment and/or spacer devices in accordance with the present disclosure may comprise any desirable shape, size or type of device, and may include one or more balloons, beads, balls, strands, coils, anchors, or other devices. Furthermore, papillary muscle adjustment devices in accordance with the present disclosure may comprise expandable structure(s), such as inflatable/expandable balloons, stents, or other structures, which may be filled with any desired or practical fluid, solid or gaseous substance in various embodiments.

In FIG. 5, the papillary muscle adjustment device 20 of FIG. 4 is shown as implanted in the left ventricle 3 (or right ventricle in another embodiment) in a position at least partially displacing the papillary muscle 15*p* away from the ventricle wall 19. The papillary muscle adjustment device 20 has been released from the delivery catheter system used to assist in implanting the device 20 in the illustrated position. In on-going operation, the placement/position of the papillary muscle adjustment device 20 may serve to reduce mitral regurgitation, as explained above.

Figure 6:
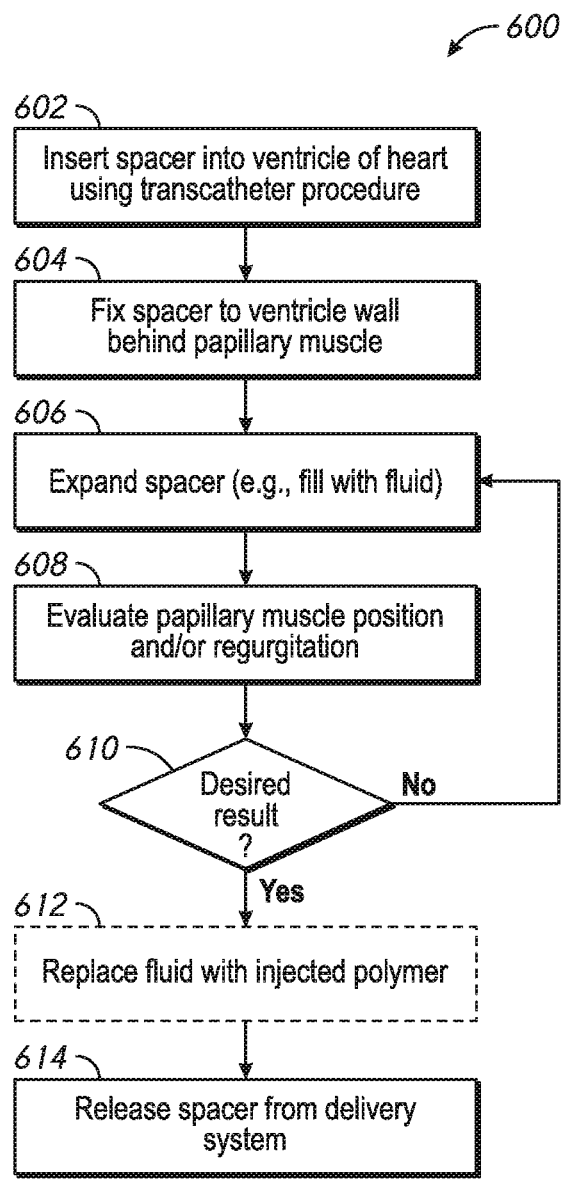
FIG. 6 is a flow diagram illustrating a process for adjusting a papillary muscle according to one or more embodiments.

FIG. 6 is a flow diagram representing a process 600 for repositioning a papillary muscle according to one or more embodiments disclosed herein. At block 602, the process 600 involves inserting a spacer device, such as a balloon, into a ventricle of the heart, such as the left ventricle, using a transcatheter procedure. For example, the spacer device may be delivered using a transfemoral, transendocardial, transcoronary, transseptal, transapical, or other approach. Alternatively, the spacer papillary muscle adjustment device may be introduced into the desired location during an open-chest surgical procedure, or using other surgical or non-surgical techniques known in the art. In accordance with certain embodiments, the spacer device (e.g., balloon) may be positioned behind one of the papillary muscles of the left (or right) ventricle.

At block 604, the process 600 involves fixing or securing the spacer device (e.g., balloon) to the ventricle wall proximate or behind the target papillary muscle. It may be desirable for the device 20 to be positioned and/or sized to not substantially obstruct normal fluid flow within the heart. The spacer device may be fixed to the ventricle wall with any suitable or desirable anchor or attachment mechanism.

At block 606, the process 600 comprises filling the spacer device with fluid or other substance, or otherwise expanding one or more components of the device, in order to expand a volume of the device or space occupied thereby. In certain embodiments, the spacer device comprises a balloon or the like, wherein the balloon is filled with a saline solution or other fluid or gas. In certain embodiments, the degree to which the target papillary muscle is re-positioned corresponds to an amount sufficient to exert pressure on the valve annulus, thereby causing a desired shift in the position of at least one of the valve leaflets and resulting in improved coaptation of the valve leaflets during closure of the valve.

The amount of fluid or gas used to fill the device may be determined by the resulting movement of the papillary muscle and/or reduction in regurgitation. At block 608, the process 600 involves evaluating papillary muscle position and/or valve regurgitation resulting from the positioning of the spacer device to determine the effectiveness of the device. At decision block 610, the process 600 involves determining whether the evaluated papillary muscle position and/or regurgitation performance evaluated/observed at block 608 is satisfactory or desirable. If not, the process 600 returns to block 606, where the spacer device may be adjusted through the additional filling, or removal of fluid or other material from the spacer device, or by otherwise adjusting the space or volume occupied by the device, to thereby further alter the effect of the device on the target papillary muscle. In certain embodiments, the operator may use echocardiography or any other suitable means to observe the movement of the valve leaflets, such as in real time. The results of the device placement may be observed continuously or at selected intervals to determine when the papillary muscle(s) has/have been repositioned sufficiently to provide a desired improvement in closure of the valve during the phase of the cardiac cycle associated with closure of the relevant valve (e.g., during systole in the case of a mitral valve). Therefore, the process 600 and/or other processes, devices and systems disclosed herein may advantageously provide a tunable device, which may be tuned while monitoring the effect of the device, such as through the use of echo or other visualization guidance.

If the desired result is achieved as determined at block 610, the process 600 continues to block 612, where fluid or filling material of the spacer device may be replaced or supplemented with a polymer or other material having desirable rigidity, firmness, and/or form, or the form or shape/size of the spacer device may otherwise be set. For example, in certain embodiments, saline solution within the balloon device may be at least partially replaced with an injected polymer.

At block 614, the process 600 involves releasing the spacer device, which has been fixed and secured within the ventricle of the heart, from the delivery system. After the fixed device (e.g., balloon) is released from the delivery system, it may continue to performs as a gap/space-maintaining form between the papillary muscle and the ventricle wall.

The process 600 and/or other processes, devices and systems disclosed herein may advantageously provide a mechanism for implementing papillary muscle adjustment using a fully transcatheter procedure on a beating heart. In certain embodiments, valve leaflets may not be substantially touched or damaged during the procedure 600. Furthermore, in certain embodiments, the spacer device may be designed to be retrievable.

Figure 7:
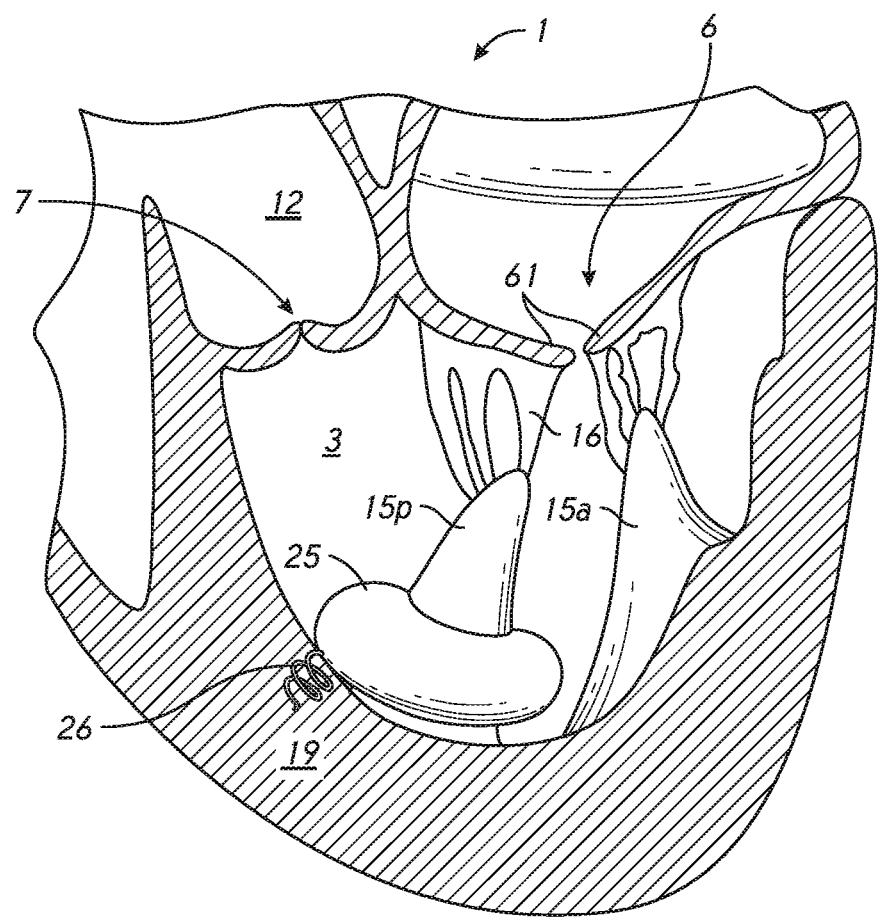
FIG. 7 illustrates a cross-section of a heart having a papillary muscle adjustment collar device implanted therein according to one or more embodiments.

FIG. 7 illustrates a cross-section of a heart 1 showing a left ventricle 3 thereof. Although certain disclosure herein is presented in the context of the left ventricle and associated anatomy (e.g., valves, papillary muscles, chordae tendineae, ventricle wall, etc.), it should be understood that the principles disclosed herein may be applicable in any ventricle of the heart (e.g., right ventricle) and associated anatomy (e.g., tricuspid valve, papillary muscles, chordae tendineae, ventricle wall, etc.).

Certain embodiments disclosed herein provide for papillary muscle adjustment using a collar or ring form 25 that may be disposed around the target papillary muscle 15$p$. The collar 25 can comprise any type of collar, ring, band, hoop, balloon or strap form that may be at least partially disposed about at least one papillary muscle, and in some cases preferably both papillary muscles. For example, the collar 25 may comprise a stiff ring-type form or a torus-shaped balloon or form, which may be polymer injected in a final state in a similar manner to the balloon spacer device shown in FIGS. 4 and 5 and described above.

The papillary muscle adjustment collar 25, which may be implanted in the left ventricle 3 (or right ventricle in another embodiment) to at least partially displace the papillary muscle 15$p$ away from the ventricle wall 19. The displacement of the papillary muscle 15$p$ from the ventricle wall 19 may help correct mitral valve insufficiency due to dysfunction or rupture of the papillary muscle. With respect to embodiments in which the papillary muscle adjustment collar 25 is implanted in the right ventricle, the device may serve to correct tricuspid regurgitation.

The placement of the collar 25 between the ventricle wall 19 and the papillary muscle 15$p$ may cause the papillary muscle 15$p$ to reposition inward, thereby lessening the traction of the chordae tendineae 16 on the corresponding leaflet of the mitral valve 6 and resulting in improved coaptation of the mitral valve leaflets 61 during closure of the valve 6. Although FIG. 7 shows repositioning of the posterior-medial papillary muscle 15$p$, it should be appreciated that the collar 25 could similarly be used to reposition the anterolateral papillary muscle 15$a$.

The delivery system for the spacer collar 25 may include a catheter for navigating the collar 25 to the desired position. For example, the collar 25 may be delivered to the implantation location in an at least partially collapsed or contracted state, wherein the collar 25 may be inflated or expanded upon arrival and/or securing in the implant chamber, such as a ventricle of the heart. The collar 25 may be inserted non-surgically in, for example, a transcatheter procedure (e.g., transfemoral procedure), wherein the collar 25, is inserted into the left ventricle 3 from the aorta 12 through the aortic valve 7 and disposed around one of the papillary muscles (e.g., posteromedial papillary muscle 15$p$). With respect to right ventricle papillary muscle adjustment, the collar 25 may be inserted into the right ventricle from the pulmonary artery through the pulmonary valve and disposed around one of the papillary muscles of the right ventricle. In certain embodiments, the collar 25 is a spacer form, such as a balloon or the like.

The spacer collar 25 may be fixed to the myocardium wall 19 of the left ventricle. The collar 25 may be fixed to the ventricle wall 19 primarily to eliminate relative movements between the collar 25 and the surrounding tissue. In certain embodiments, the spacer collar 25 may be fixed to the left ventricle wall 19 using an anchor or attachment member 26. Once positioned and/or fixed, the collar 25 may be expanded or inflated to a desirable size. For example, the collar 25 may comprise a balloon that may be filled with fluid, such as a saline solution or a gaseous solution, through a catheter (not shown). In certain embodiments, the desired position of the collar 25 and/or the amount of expansion of the collar 25 through fluid infusion or other means may be determined by the resulting movement of the papillary muscle and/or the reduction in mitral (or tricuspid) regurgitation performance, which may be observed using echocardiography or other means. With regard to a fluid-filled collar device, when it is determined that the result is satisfactory, the fluid (e.g., saline solution) may be replaced with an injected polymer.

Figure 8:
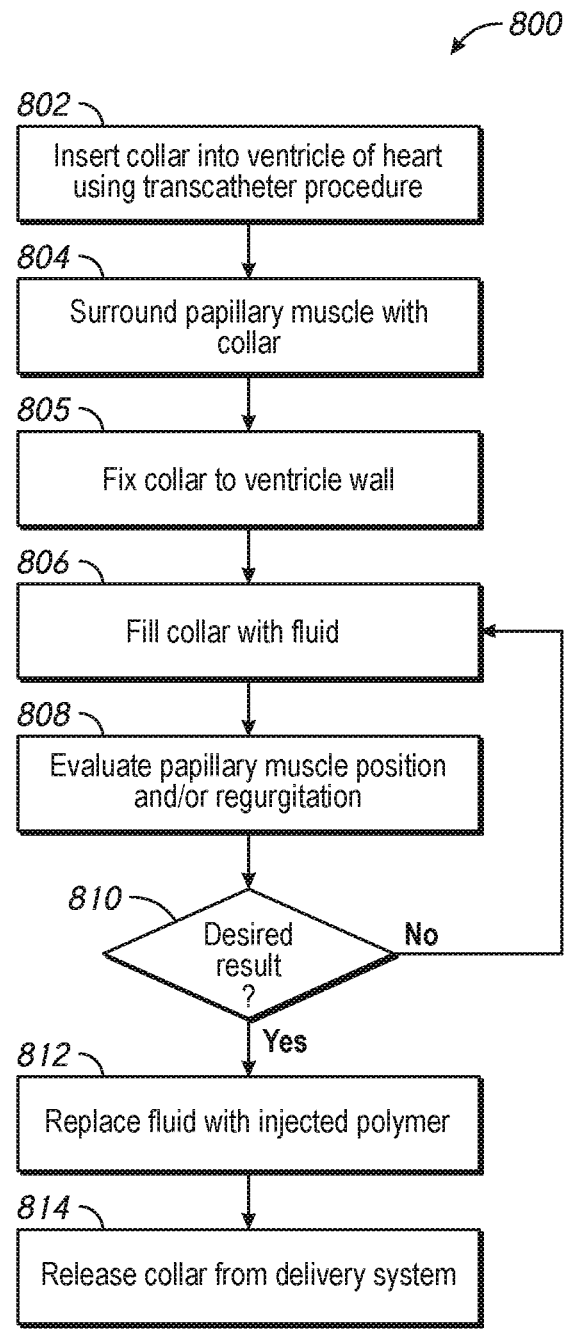
FIG. 8 is a flow diagram illustrating a process for adjusting a papillary muscle according to one or more embodiments.

FIG. 8 is a flow diagram representing a process 800 for adjusting and/or repositioning a papillary muscle according to one or more embodiments disclosed herein. At block 802, the process 800 involves inserting a collar-type spacer device, such as a balloon, into a ventricle of the heart, such as the left ventricle, using a transcatheter procedure. For example, the collar device may be delivered using a transfemoral, transendocardial, transcoronary, transseptal, transapical, or other procedure/approach. Alternatively, the papillary muscle adjustment collar may be introduced into the desired location during an open-chest surgical procedure, or using other surgical or non-surgical techniques known in the art. In accordance with certain embodiments, the collar device (e.g., balloon) may be disposed or wrapped around one of the papillary muscles of the left (or right) ventricle, as shown at block 804.

At block 805, the process 800 involves fixing or securing the collar device (e.g., balloon) to the ventricle wall proximate or behind the target papillary muscle. It may be desirable for the collar to be positioned and/or sized to not substantially obstruct normal fluid flow within the heart. The collar may be fixed to the ventricle wall with any suitable or desirable anchor or attachment mechanism.

At block 806, the process 800 comprises filling the collar device with fluid or other substance, or otherwise expanding one or components of the device, in order to expand a volume of the collar or space occupied thereby. As the collar fills, it may displace the target papillary muscle in a direction away from the adjacent ventricle wall. In certain embodiments, the collar device comprises a balloon or the like, wherein the balloon is filled with a saline solution or other fluid or gas. In certain embodiments, the degree to which the target papillary muscle is re-positioned corresponds to an amount sufficient to exert pressure on the valve annulus, thereby causing a desired shift in the position of at least one of the valve leaflets and resulting in improved coaptation of the valve leaflets during closure of the valve.

The amount of fluid or gas used to fill the collar may be determined by the resulting movement of the papillary muscle and/or reduction in regurgitation. At block 808, the process 800 involves evaluating papillary muscle position and/or valve regurgitation resulting from the positioning of the collar device to determine the effectiveness of the device. At decision block 810, the process 800 involves determining whether the evaluated papillary muscle position and/or regurgitation performance observed at block 808 is satisfactory or desirable. If not, the process 800 returns to block 808, where the collar spacer device may be adjusted through the additional filling, or removal of fluid or other material from the collar, or by otherwise adjusting the space or volume occupied by the collar, to thereby further alter the effect of the device on the target papillary muscle. In certain embodiments, the operator may use echocardiography or any other suitable means to observe the movement of the valve leaflets, such as in real time. The results of the device placement may be observed continuously or at selected intervals to determine when the papillary muscle(s) has/have been repositioned sufficiently to provide a desired improvement in closure of the valve during the phase of the cardiac cycle associated with closure of the relevant valve (e.g., during systole in the case of a mitral valve). Therefore, the process 800 and/or other processes, devices and systems disclosed herein may advantageously provide a tunable device, which may be tuned while monitoring the effect of the device, such as through the use of echo or other visualization guidance.

If the desired result is achieved as determined at block 810, the process 800 continues to block 812, where the fluid or filling material of the collar device may be replaced or supplemented with a polymer or other material having desirable rigidity and/or form. For example, in certain embodiments, saline solution within the collar may be at least partially replaced with an injected polymer.

At block 814, the process 800 involves releasing the collar device, which has been fixed and secured within the ventricle of the heart, from the delivery system. After the fixed collar is released from the delivery system, it may continue to perform as a gap/space-maintaining form between the papillary muscle and the ventricle wall.

The process 800 and/or other processes, devices and systems disclosed herein may advantageously provide a mechanism for implementing papillary muscle adjustment using a fully transcatheter procedure on a beating heart. In certain embodiments, valve leaflets may not be substantially touched or damaged during the procedure 800. Furthermore, in certain embodiments, the collar device may be designed to be retrievable.

Figure 9:
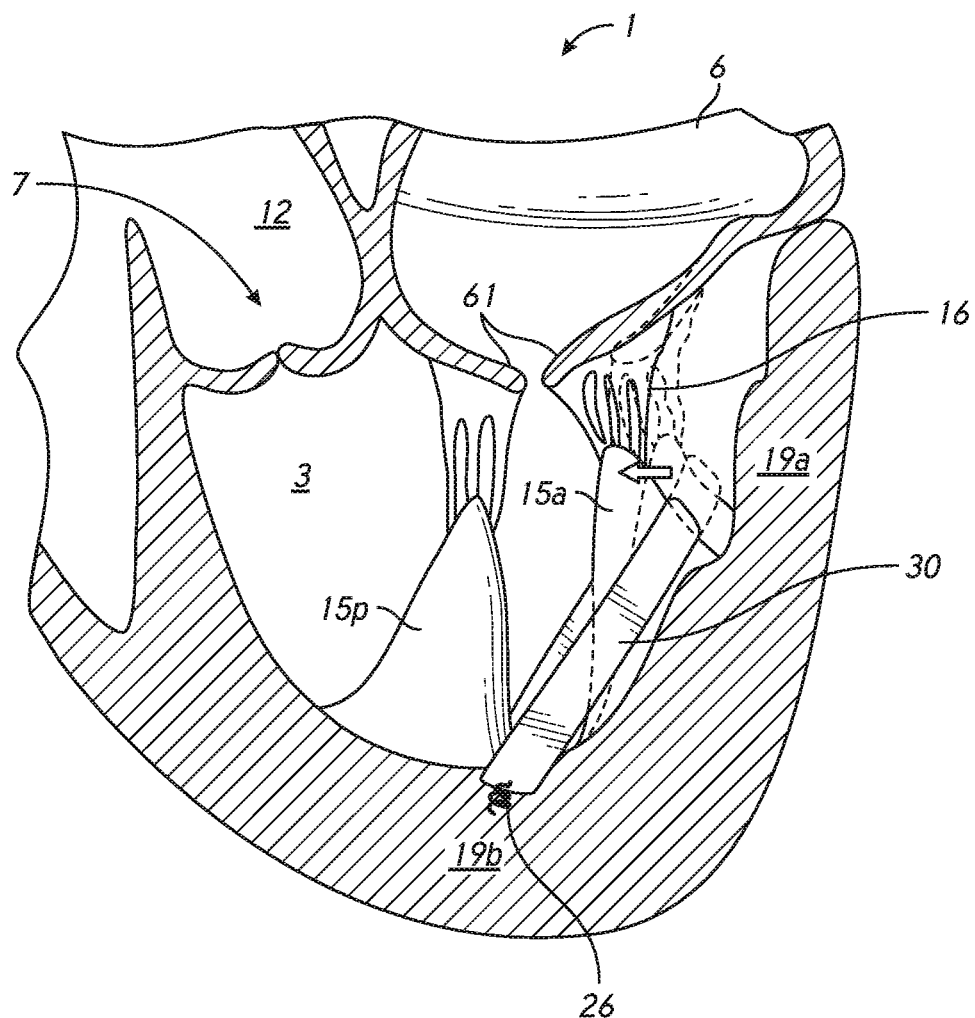
FIG. 9 illustrates a cross-section of a heart having a papillary muscle adjustment strap implanted therein according to one or more embodiments.

FIG. 9 illustrates a cross-section of a heart 1 showing a left ventricle 3 thereof. Although certain disclosure herein is presented in the context of the left ventricle and associated anatomy (e.g., valves, papillary muscles, chordae tendineae, ventricle wall, etc.), it should be understood that the principles disclosed herein may be applicable in any ventricle of the heart (e.g., right ventricle) and associated anatomy (e.g., tricuspid valve, papillary muscles, chordae tendineae, ventricle wall, etc.). Certain embodiments disclosed herein provide for papillary muscle adjustment through the use of a strap member 30. The term "strap" is used herein according to its broad and ordinary meaning and may be used in certain contexts herein to refer to any strap-type form, device, or member, or any other type of tether, collar, band, cord, or the like.

FIG. 9 shows a papillary muscle adjustment strap 30, which may be implanted in the left ventricle 3 (or right ventricle in another embodiment) to at least partially displace the papillary muscle 15a away from the ventricle wall 19a. The displacement of the papillary muscle 15a from the ventricle wall 19a may help correct mitral valve insufficiency due to dysfunction or rupture of the papillary muscle. With respect to embodiments in which the papillary muscle adjustment strap 30 is implanted in the right ventricle, the device may serve to correct tricuspid regurgitation.

The positioning of the strap 30 around the papillary muscle 15a as illustrated may pull on the papillary muscle 15a and cause the papillary muscle 15a to reposition inward, thereby lessening the traction of the chordae tendineae on the corresponding leaflet of the mitral valve, thereby resulting in improved coaptation of the mitral valve leaflets during closure of the valve. Although FIG. 9 shows repositioning of the anterolateral papillary muscle 15a, it should be appreciated that the strap 30 may similarly be used to reposition the posterior-medial papillary muscle 15p, such as by wrapping the strap 30 around the outer periphery of the papillary muscle 15p and fixing the strap 30 to a portion of the ventricle wall opposite the papillary muscle a5p to thereby pull the papillary muscle 15p inward. In certain embodiments, one or more strap devices may be used to pull both papillary muscles inward to further improve coaptation.

The strap 30 may be introduced into the ventricle 3 and implanted therein using a delivery system (not shown), which may include a catheter 24 for navigating the strap 30 to the desired position. For example, the strap 30 may be delivered to the implantation location in an at least partially rolled-up, contracted, or compressed state, wherein the strap 30 may be extended upon arrival in the implant chamber, such as a ventricle of the heart. The strap 30 may be inserted non-surgically in, for example, a transcatheter procedure (e.g., transfemoral procedure), wherein the strap 30, is inserted into the left ventricle 3 from the aorta 12 through the aortic valve 7 and wrapped around one of the papillary muscles (e.g., anterolateral papillary muscle 15a). With respect to right ventricle papillary muscle adjustment, the strap 30 may be inserted into the right ventricle from the pulmonary artery through the pulmonary valve and wrapped around or attached to one of the papillary muscles of the right ventricle. In certain embodiments, the strap 30 is a band-type form. Although the strap 30 is shown as a band-shaped strap wrapped around the papillary muscle 15a, in certain embodiments, the strap may not be wrapped around the papillary muscle, but may be otherwise attached to the papillary muscle. For example, the strap 30 may include a papillary muscle-puncturing suture or anchor that may allow for the strap 30 to create tension that pulls the papillary muscle inward, as shown. In certain embodiments, the strap 30 is a cord that punctures the papillary muscle and pulls the papillary muscle inward.

The strap 30 may be fixed to the myocardium wall of the left ventricle at one or both ends. In certain embodiments, the strap 30 may be fixed to the left ventricle wall using an anchor or attachment member 26. The strap 30 may be tightened or loosened in order to modify the degree to which the papillary muscle 15a is pulled or displaces. In certain embodiments, the strap 30 may be tightened or loosened based on the positioning of the fixing anchor(s) 26 with respect to the ventricle wall 19b and/or strap 30. In certain embodiments, the desired position of the strap 30 and/or the amount of tension in the strap 30 may be determined by the resulting movement of the papillary muscle and/or the reduction in mitral (or tricuspid) regurgitation performance, which may be observed using echocardiography or other means. In certain embodiments, the strap may be fixed to the ventricle wall at a location 19b at least partially between the papillary muscles 15p, 15a.

Figure 10:
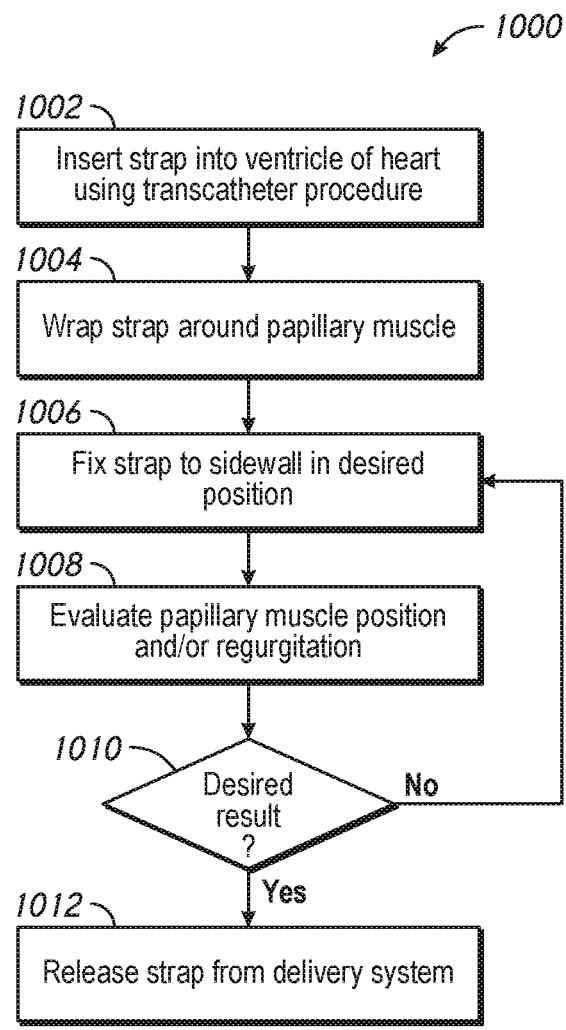
FIG. 10 is a flow diagram illustrating a process for adjusting a papillary muscle according to one or more embodiments.

FIG. 10 is a flow diagram illustrating a process 1000 for adjusting a papillary muscle of a heart in order to reduce regurgitation in accordance with one or more embodiments disclosed herein. At block 1002, the process 1000 involves inserting a strap member into a ventricle of the heart, such as the left ventricle, using a transcatheter procedure or the like. At block 1004, the process 1000 involves surrounding a target papillary muscle within the ventricle with the strap member.

At block 1006, the process 1000 involves fixing the strap member at one or more ends thereof to a wall or other tissue portion of the ventricle in a desired position and/or tension in order to effect a repositioning of the papillary muscle by pulling the papillary muscle towards one or more ends the strap member. In certain embodiments, the strap may be fixed to the ventricle wall at a location at least partially between the papillary muscles. At block 1008, the process 1000 involves evaluating papillary muscle position and/or regurgitation, and further, at decision block 1010, determining whether the evaluated results are satisfactory or desirable. If not, the process 1000 returns to block 1006 where the strap member may be adjusted, such as by adjusting a length or fixation point of the strap member.

If the desired results are achieved at block 1010, the process 1000 continues to block 1012, where the strap member may be released from the delivery system and maintained in the heart ventricle for ongoing papillary muscle positioning.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A method for treating a heart valve, said method comprising:
    delivering a spacer device into a ventricle of a heart using a delivery system;
    anchoring the spacer device to an interior wall of the ventricle at least in part by inserting an anchor coupled to the spacer device into myocardial tissue associated with the interior wall of the ventricle;
    inflating the spacer device with fluid to thereby expand the spacer device between a papillary muscle disposed in the ventricle and a surface of the interior wall of the ventricle, the papillary muscle being connected to a leaflet of an atrioventricular heart valve via chordae tendineae; and
    releasing the spacer device from the delivery system.

2. The method of claim 1, wherein performing the method improves at least one of prolapse of the leaflet and regurgitation of the heart valve.

3. The method of claim 1, wherein the ventricle is a left ventricle of the heart and the heart valve is a mitral valve.

4. The method of claim 1, wherein the fluid comprises saline.

5. The method of claim 1, further comprising:
after said inflating the spacer device, determining whether function of the heart valve is adequate; and
when it is determined that the function of the heart valve is not adequate, adjusting the spacer device prior to said releasing the spacer device from the delivery system.

6. The method of claim 5, wherein said determining whether function of the heart valve is adequate comprises determining whether the papillary muscle has moved to a desirable position.

7. The method of claim 5, wherein said determining whether function of the heart valve is adequate comprises determining whether regurgitation of the heart valve has been sufficiently reduced.

8. The method of claim 5, wherein said determining whether function of the heart valve is adequate comprises determining whether a position of the leaflet has moved to a desirable position.

9. The method of claim 5, wherein said adjusting the spacer device comprises further inflating the spacer device to further reposition the papillary muscle.

10. The method of claim 1, further comprising:
after said inflating the spacer device with fluid, determining whether heart valve regurgitation has been reduced to a predetermined level;
when it is determined that heart valve regurgitation has not been reduced to the predetermined level, adjusting an amount of fluid in the spacer device; and
when it is determined that heart valve regurgitation has been reduced to the predetermined level, at least partially replacing the fluid with a polymer.

11. The method of claim 10, wherein said determining whether heart valve regurgitation has been reduced to the predetermined level is performed at least part using echocardiography.

12. The method of claim 1, wherein said delivering the spacer device into the ventricle of the heart is performed using a transcatheter procedure.

13. The method of claim 12, wherein the transcatheter procedure is a transfemoral procedure.

14. A method for treating a heart valve, said method comprising:
delivering a spacer device into a ventricle of a heart using a delivery system;
anchoring the spacer device to an interior wall of the ventricle;
at least partially surrounding a papillary muscle disposed in the ventricle with the spacer device;
inflating the spacer device with fluid to thereby expand the spacer device between the papillary muscle and a surface of the interior wall of the ventricle, the papillary muscle being connected to a leaflet of an atrioventricular heart valve via chordae tendineae; and
releasing the spacer device from the delivery system.

15. The method of claim 14, wherein the spacer device comprises a collar form.

16. The method of claim 14, wherein the spacer device comprises a torus-shaped balloon.

17. The method of claim 14, further comprising replacing the fluid with an injected polymer.

18. The method of claim 14, further comprising:
placing a second spacer device at least partially around a second papillary muscle in the ventricle; and
inflating the second spacer device to displace the second papillary muscle.

* * * * *